(12) United States Patent
Von Dach et al.

(10) Patent No.: US 7,813,520 B2
(45) Date of Patent: Oct. 12, 2010

(54) HEARING DEVICE AND METHOD FOR SUPPLYING AUDIO SIGNALS TO A USER WEARING SUCH HEARING DEVICE

(75) Inventors: Thomas Von Dach, Cressier (CH); Samuel Harsch, Ballaigues (CH)

(73) Assignee: Phonak AG, Staefa (CH)

( * ) Notice: Subject to any disclaimer, the term of this patent is extended or adjusted under 35 U.S.C. 154(b) by 1125 days.

(21) Appl. No.: 11/457,188

(22) Filed: Jul. 13, 2006

(65) Prior Publication Data
US 2008/0013744 A1    Jan. 17, 2008

(51) Int. Cl.
H04R 25/00    (2006.01)
H04B 15/00    (2006.01)
H03G 3/00    (2006.01)

(52) U.S. Cl. .................. 381/372; 381/94.1; 381/104

(58) Field of Classification Search .............. 381/60, 381/71.6, 72, 83, 93, 94.1, 312, 317, 318, 381/321, 328, 372, 380, 104, 107
See application file for complete search history.

(56) References Cited

U.S. PATENT DOCUMENTS

| | | | |
|---|---|---|---|
| 4,307,385 A | | 12/1981 | Evans et al. |
| 4,455,675 A | | 6/1984 | Bose et al. |
| 5,577,511 A | | 11/1996 | Killion |
| 5,631,965 A | * | 5/1997 | Chang et al. .................. 381/72 |
| 6,567,524 B1 | * | 5/2003 | Svean et al. ................. 381/71.6 |
| 6,687,377 B2 | | 2/2004 | Voix et al. |
| 6,741,707 B2 | | 5/2004 | Ray et al. |
| 7,406,179 B2 | | 7/2008 | Ryan |
| 2004/0086138 A1 | | 5/2004 | Kuth |

FOREIGN PATENT DOCUMENTS

| | | |
|---|---|---|
| DE | 10117705 A1 | 10/2001 |
| EP | 1 594 344 A2 | 11/2005 |
| WO | 2005 046543 A1 | 5/2005 |

\* cited by examiner

*Primary Examiner*—Brian Ensey
(74) *Attorney, Agent, or Firm*—Roberts Mlotkowski Safran & Cole, P.C.; David S. Safran

(57) ABSTRACT

There is provided a hearing system comprising: a hearing device to be worn at or in a user's ear for supplying audio signals to said user and comprising a sound attenuation portion for attenuating ambient sound before reaching the user's ear, means for producing audio signals at a controlled level, a loudspeaker which is included in the attenuation portion and which is oriented towards the user's ear canal for providing sound corresponding to the audio signal produced by the audio signal producing means to the user's ear canal, a microphone which is included in the attenuation portion and which is oriented towards the user's ear canal for capturing audio signals from the sound provided by the loudspeaker to the user's ear canal, and a level control unit adapted to control the level of the audio signals produced by the audio signal producing means according to the audio signals captured by the microphone.

13 Claims, 3 Drawing Sheets

HEARING DEVICE AND METHOD FOR SUPPLYING AUDIO SIGNALS TO A USER WEARING SUCH HEARING DEVICE

BACKGROUND OF THE INVENTION

1. Field of the Invention

The invention relates to a method for supplying audio signals to a user wearing a hearing device at or in his ear, which comprises a sound attenuation portion for attenuating ambient sound before reaching the user's ear drum with the sound attenuation portion comprising a loudspeaker which is oriented towards the user's ear canal.

2. Description of Related Art

Such a hearing device may be a headphone or an earphone which is used for listening, for example, to music from a portable audio source, such as an MP3 player or a CD player. Usually such audio devices have a manual volume control which is operated by the user of the device according to the desired sound pressure level. One problem encountered with such devices is that the users of such portable audio devices, especially if young people, are tending to use the device at sound pressure levels which may create a hearing damage.

Active hearing protection devices comprise an active communication unit consisting of a microphone for capturing ambient sound, an audio signal processing unit and a loudspeaker for reproducing the sound captured by the microphone to the user's ear according to audio signal processing in the processing unit. Such active hearing protection devices, and also hearing aids, usually comprise some kind of level limitation which is based on the level of the input audio signals to the signal processing unit as provided by the microphone in order to limit the sound pressure level created by the loudspeaker to values which are not dangerous for the user's hearing.

U.S. Pat. No. 6,567,524 B1 relates to an earplug comprising a loudspeaker oriented towards the user's ear canal and a microphone connected to the user's ear canal via a sound passage in order to capture sound in the user's ear canal. According to one embodiment, the earplug may be used as a headphone coupled to a CD player in order to monitor the noise dose submitted from the headphones to the ear over time or in peaks. To this end, the earplug is provided with a signal processing unit.

DE 101 12 305 A1 relates to a hearing protection device comprising an earplug including a microphone oriented towards the user's ear canal for capturing sound in the ear canal and optionally a loudspeaker for providing audio signals to the user. The microphone is connected to a signal processing unit in order to measure in-situ the sound pressure level acting on the user's ear protected by the earplug. If the sound pressure level is found to be too high the device may take corresponding counter-measures in order to protect the user's hearing from damages. An example of such a counter measure is to act on the machine creating the noise.

It is also known to provide a hearing protection device, such as a headphone or an earplug, with a microphone oriented towards the user's ear canal for picking up sound in the ear canal, an audio signal processing unit and a loudspeaker oriented towards the user's ear canal for performing active noise reduction (ANR) wherein the loudspeaker is used for creating a phase-shifted anti-noise signal. Examples for such ANR hearing protection devices are given in WO 2005/046543 A1, U.S. Pat. No. 6,741,707 B2 and DE 101 17 705 A1.

U.S. Pat. No. 6,689,377 B2 relates to a method for measuring the acoustic attenuation provided by a customized earplug, wherein the earplug is provided with a sound bore extending from the outer side of the earplug to the inner end of the earplug, wherein a remote device is inserted into the outer end of the sound bore, which remote device comprises a first microphone oriented towards the sound bore and a second microphone oriented towards ambience, and wherein test sound is provided by an external loudspeaker. Both the loudspeaker and the remote device are connected to a computer unit on which a measurement program is run. The acoustic attenuation provided by the earplug is calculated from the sound level difference between the first microphone and the second microphone.

U.S. Pat. No. 5,577,511 relates to a method for measuring in-situ the acoustic attenuation provided by an earplug, wherein a probe tube extends through the earplug into the ear canal and wherein the outer end of the probe tube is connected to a first microphone, while a second microphone is provided at the ear for measuring sound pressure levels exterior to the ear canal as a reference microphone. The acoustic attenuation provided by the earplug is calculated from the difference of the sound levels measured by the first and the second microphone. The test sound for the measurement is the user's voice.

It is an object of the invention to provide for a method for supplying audio signals to a user by an ear-worn hearing device comprising a sound attenuation portion with a loudspeaker, wherein the user's ear should be protected from damages. It is a further object to provide for a corresponding hearing system.

SUMMARY OF THE INVENTION

According to the invention these objects are achieved by a method and a hearing system as described here.

The invention is beneficial in that, by capturing audio signals by a microphone which is included in the attenuation portion of the hearing device and which is oriented towards the user's ear canal from the sound provided by the loudspeaker to the user's ear canal and by controlling the level of the audio signal provided to the loudspeaker according to the audio signals captured by the microphone, the sound level in the user's ear canal generated by the loudspeaker can be accurately measured and controlled in order to avoid sound pressure levels which may damage the user's ear. Thereby an accurate and effective automatic sound pressure level control is realized.

These and further objects, features and advantages of the present invention will become apparent from the following description when taken in connection with the accompanying drawings which, for purposes of illustration only, show several embodiments in accordance with the present invention.

DETAILED DESCRIPTION OF THE INVENTION

Figure 1:
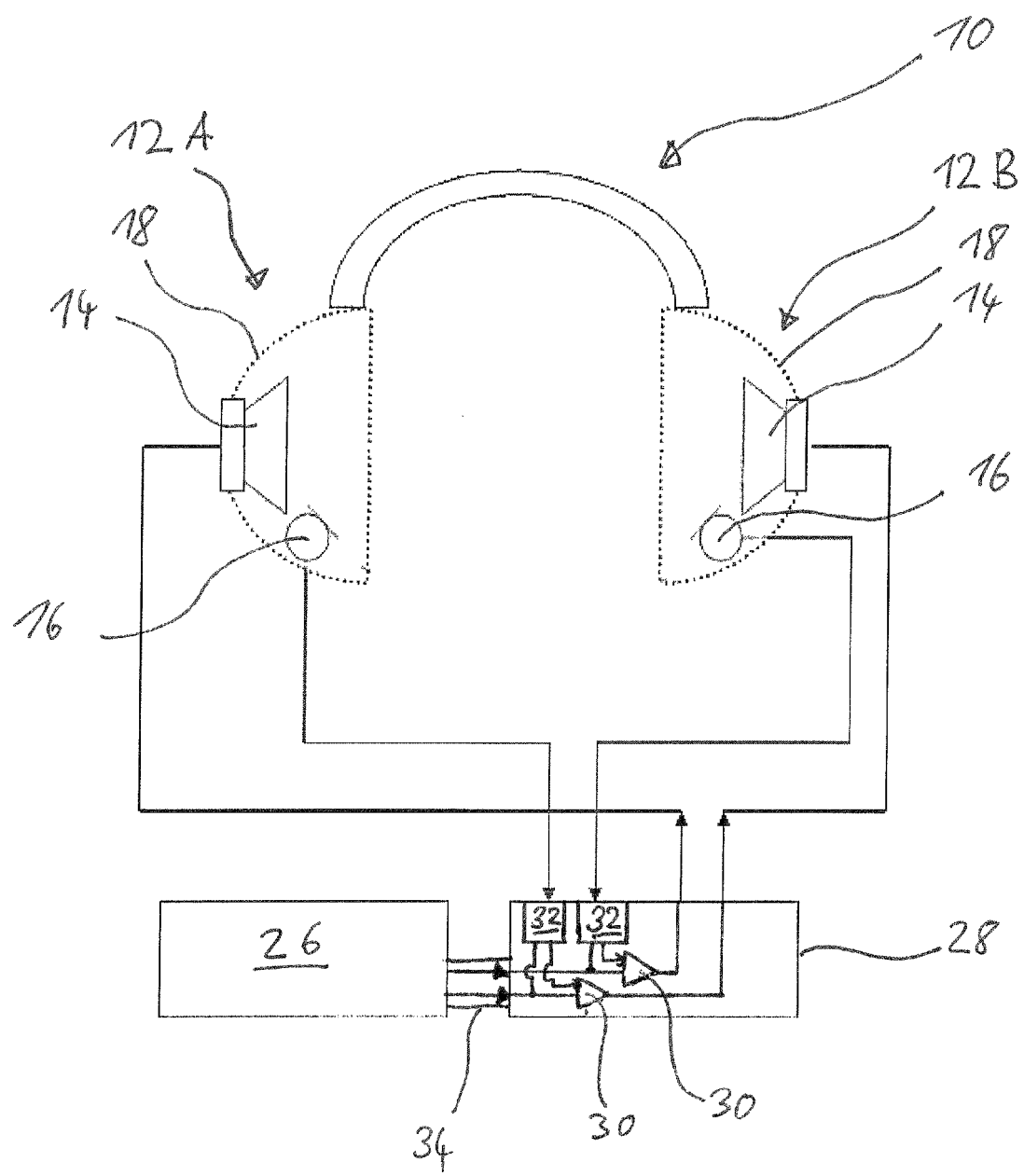
FIG. 1 shows schematically an example of a hearing system according to the invention.
Figure 2:
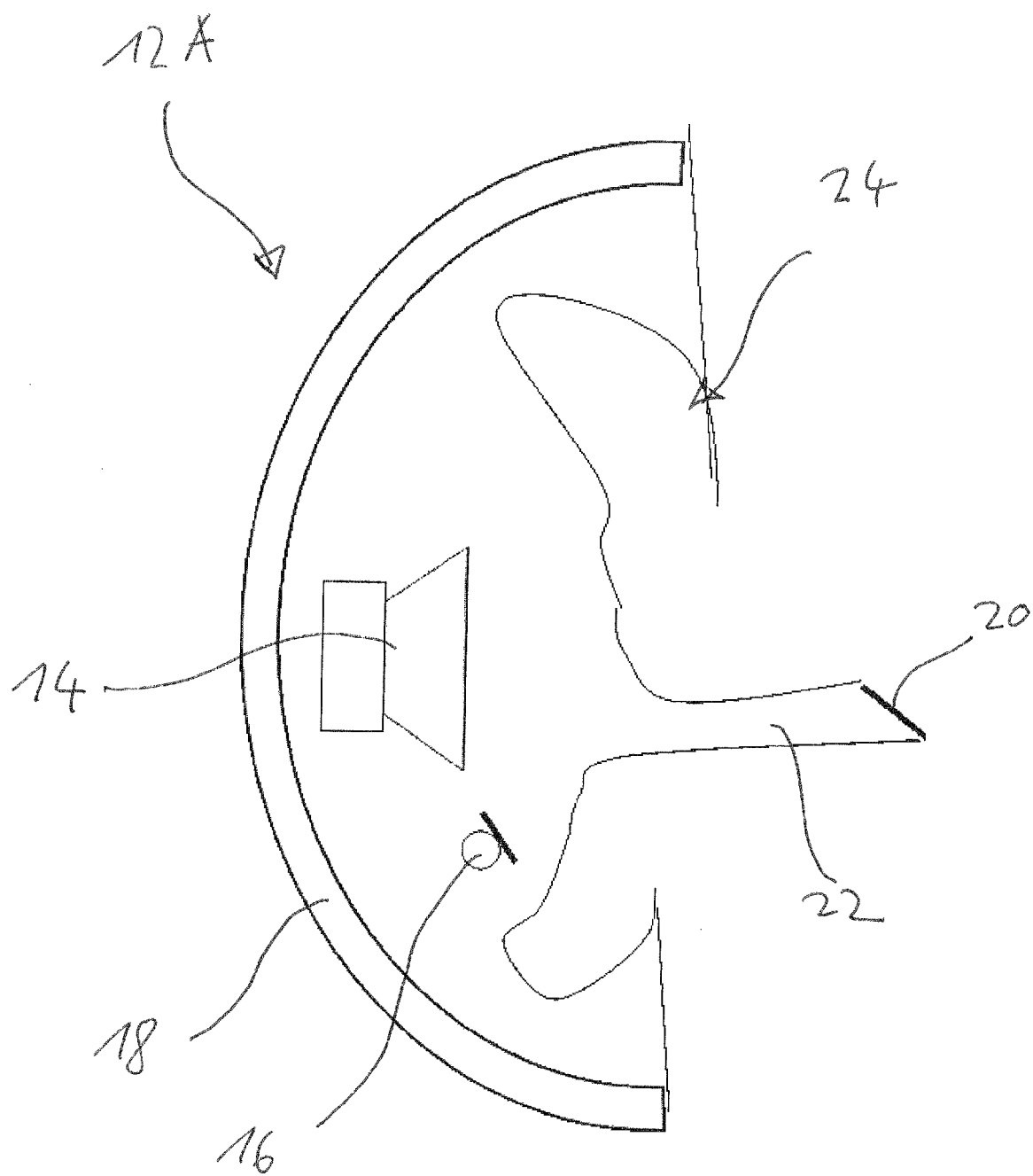
FIG. 2 is a more detailed view of one of ear of the user when wearing a hearing device according to the invention.

In FIG. 1 an example of a hearing system according to the invention is schematically shown, which comprises as a hearing device a headphone 10 comprising a left ear cup 12A and a right ear cup 12B. Each cup 12A, 12B comprises at least one loudspeaker 14 and a microphone 16, which both are included in the cup 12A, 12B. Each cup 12A, 12B comprises a housing 18 which acts as a sound attenuation portion for attenuating ambient sound before reaching the user's ear drum 20. The at least one loudspeaker 14 is oriented towards the user's ear canal 22 when the headphone 10 is worn at the user's ears 24 in order to provide sound to the user's ear canal 22.

The microphone 16 likewise is oriented towards the user's ear canal 22 in order to pick up sound in the user's ear canal 22 and to capture a corresponding audio signal representative of the sound level in the user's ear canal 22.

According to FIG. 1, the system in addition to the headphone 10 comprises a preferably portable audio device 26 having a headphone output, such as an MP3 player or a CD player, which serves as an audio signal source. The headphone 10 is connected to the audio device 26 via an audio signal processing unit 28 which processes the audio signals received from the audio device 26 in order to be reproduced by the loudspeakers 14 of the headphone 10. The audio signal processing unit 28 may integrated into the headphone 10 or it may be worn somewhere at the user's body separate from the headphone 10 or it may be part of the audio amplifier of the audio device 26. Usually the audio signal processing unit 28 will include an interface 34, such a wire connection, for receiving audio signals from an audio signal source, such as from the audio device 26.

Usually the audio signal provided by the audio device 26 will be a stereo signal. Each of the two channels of the stereo signal will be amplified by a variable gain amplifier 30 which via a control unit 32 is controlled according to the audio signals captured by the microphones 16. To this end, the audio signals from the microphones 16 are provided to the audio signal processing unit 28. For example, the control units 32 may be programmed or designed such that a predetermined upper limit of the level of the audio signals captured by the microphones 16 is not exceeded. This upper limit not to be exceeded may be, for example, 95 dB. To achieve such automatic volume control, the control unit 32 will set the gain applied by the variable gain amplifier 30 in such a manner that the sound pressure level in the ear canal 22 as measured by the microphone 16, which is primarily caused by the sound from the loudspeaker 18 does not exceed said predetermined upper limit. In other words, the level of the audio signals produced by the audio signal processing unit 28 is controlled according to the level of the audio signals captured by the microphones 16.

In addition to providing for such automatic, i.e. closed loop, volume control, the audio signal processing unit 28 also may serve to record the level of the audio signals captured by the microphones 16 as a function of time, thereby acting as a dosimeter. In this case, an alarm signal may be issued by the audio signal processing unit 28, for example as an alarm tone or an alarm message provided to the user via the loudspeakers 14, if a predetermined upper limit of the level of the audio signals captured by the microphones 16 is reached and/or if a predetermined upper limit of the time-integrated level of the audio signals captured by the microphones 16 is reached.

Figure 3:
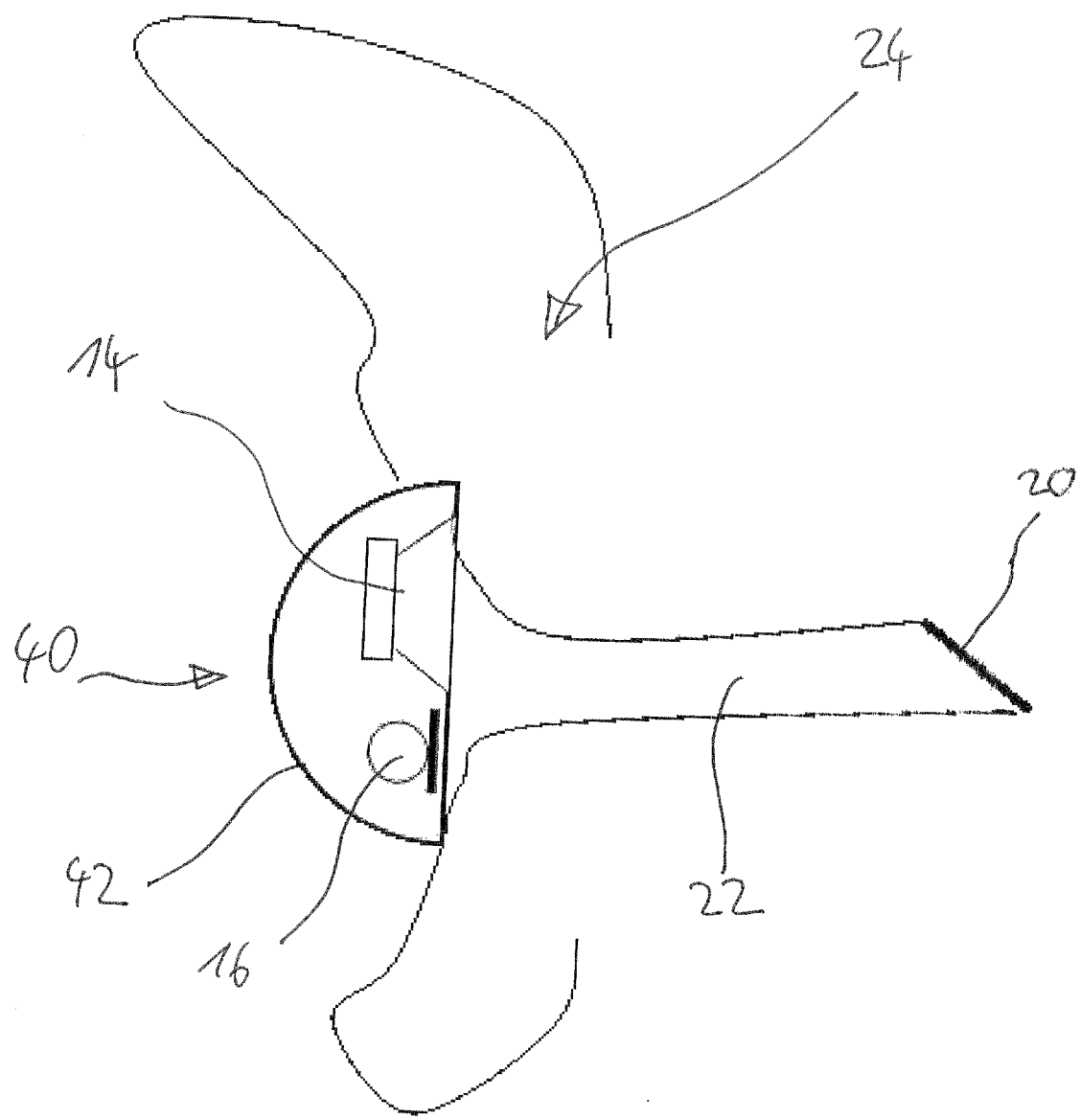
FIG. 3 is a view like FIG. 2, with an alternative embodiment of a hearing device according to the invention being shown.

In the embodiment shown in FIG. 3 the headphone 10, i.e. the cups 12A, 12B of the headphone 10, may be replaced by an earplug 40 for each ear of the user, which comprises a shell 42 having an outer shape which is appropriate for being received in the user's ear 24. In this case, the loudspeaker 14 and the microphones 16 are integrated into the shell 42 in such manner that they are both oriented towards the user's ear canal 22 when the earplug 40 is worn at the user's ear 24. Usually the user will wear another earphone 40 at the other ear in order to achieve stereo presentation of the audio signal.

The earplugs 40 will be connected to the audio signal processing unit 28 in a similar manner as shown in FIG. 1 for the headphone 10.

While various embodiments in accordance with the present invention have been shown and described, it is understood that the invention is not limited thereto, and is susceptible to numerous changes and modifications as known to those skilled in the art. Therefore, this invention is not limited to the details shown and described herein, and includes all such changes and modifications as encompassed by the scope of the appended claims.

What is claimed is:

1. A method for supplying audio signals to a user wearing a hearing device at or in an ear, said hearing device comprising a sound attenuation portion for attenuating ambient sound before reaching an ear drum of said user, the method comprising:
    producing an audio signal at a controlled level by audio signal producing means;
    providing sound corresponding to said audio signal produced by said audio signal producing means to an ear canal of said user by a loudspeaker which is included in said attenuation portion and which is oriented towards said user's ear canal;
    capturing audio signals by a microphone, which is included in said attenuation portion and which is oriented towards said user's ear canal, from said sound provided by said loudspeaker to said user's ear canal;
    wherein a level of said audio signal produced by said audio signal producing means is controlled according to said audio signals captured by said microphone, and
    wherein an automatic, closed loop, volume control is performed by which said level of said audio signals produced by said audio signal producing means is limited in such a manner that a predetermined upper limit of said level of said audio signals captured by said microphone is not exceeded.

2. The method of claim 1, wherein said level of said audio signals captured by said microphone is recorded as a function of time.

3. The method of claim 2, wherein an alarm signal is issued by said hearing device if a predetermined upper limit of said level of said audio signals captured by said microphone is reached.

4. The method of claim 1, wherein said upper limit of said level of said audio signals captured by said microphone, which is not to be exceeded, is 95 dB.

5. The method of claim 1, wherein an alarm signal is issued by said hearing device if a predetermined upper limit of a time-integrated level of said audio signals captured by said microphone is reached.

6. A hearing system comprising: a hearing device to be worn at or in an ear of a user for supplying audio signals to said user and comprising a sound attenuation portion for attenuating ambient sound before reaching said user's ear, means for producing audio signals at a controlled level, a loudspeaker which is included in said attenuation portion and which is oriented towards an ear canal of said user for providing sound corresponding to said audio signal produced by said audio signal producing means to said user's ear canal, a microphone which is included in said attenuation portion and which is oriented towards said user's ear canal for capturing audio signals from said sound provided by said loudspeaker to said user's ear canal, and a level control unit adapted to control a level of said audio signals produced by said audio signal producing means according to said audio signals captured by said microphone wherein said audio signal producing means comprise means for automatic, closed loop, volume control that limits the level of the audio signal produced in such a manner that a predetermined upper limit of the level of said audio signals captured by said microphone is not exceeded.

7. The hearing system of claim 6, wherein said audio signal producing means comprise a variable gain amplifier.

8. The hearing system of claim 7, wherein said audio signal producing means comprise a control unit for controlling said variable gain amplifier according to said audio signals captured by said microphone.

9. The hearing system of claim 6, wherein said hearing device is one of two cups of a headphone.

10. The hearing system of claim 6, wherein said hearing device is an earphone.

11. The hearing system of claim 6, wherein said audio signal producing means comprise an interface for receiving audio signals from an audio signal source.

12. The hearing system of claim 11, wherein said audio signal source is a portable music player.

13. The hearing system of claim 11, wherein said audio signal source is an audio amplifier.

* * * * *